(12) United States Patent
John et al.

(10) Patent No.: US 8,968,784 B2
(45) Date of Patent: Mar. 3, 2015

(54) METHOD FOR PREPARING HYDRO/ORGANO GELATORS FROM DISACCHARIDE SUGARS BY BIOCATALYSIS AND THEIR USE IN ENZYME-TRIGGERED DRUG DELIVERY

(75) Inventors: George John, Edison, NJ (US); Praveen Vemula, Cambridge, MA (US)

(73) Assignee: Research Foundation of the City University of New York, New York, NY (US)

( * ) Notice: Subject to any disclaimer, the term of this patent is extended or adjusted under 35 U.S.C. 154(b) by 867 days.

(21) Appl. No.: 12/313,784

(22) Filed: Nov. 24, 2008

(65) Prior Publication Data

US 2010/0129451 A1 May 27, 2010
US 2014/0037731 A9 Feb. 6, 2014

Related U.S. Application Data

(63) Continuation of application No. PCT/US2007/012333, filed on May 22, 2007.

(60) Provisional application No. 60/802,412, filed on May 22, 2006.

(51) Int. Cl.
| | |
|---|---|
| *A61K 9/14* | (2006.01) |
| *A61K 31/05* | (2006.01) |
| *A01N 31/08* | (2006.01) |
| *A61K 9/06* | (2006.01) |
| *A61K 47/26* | (2006.01) |

(52) U.S. Cl.
CPC . *A61K 31/05* (2013.01); *A61K 9/06* (2013.01); *A61K 47/26* (2013.01)
USPC .......................................... 424/488; 514/733

(58) Field of Classification Search
CPC .......... A61K 47/26; A61K 31/05; A61K 9/06

USPC .......................................... 424/488; 514/733
See application file for complete search history.

(56) References Cited

U.S. PATENT DOCUMENTS

| | | | | |
|---|---|---|---|---|
| 5,262,313 | A | 11/1993 | Kitchell et al. | 435/135 |
| 6,342,238 | B1 | 1/2002 | Simonnet et al. | 424/401 |
| 2002/0136769 | A1 | 9/2002 | Kabanov et al. | 424/487 |
| 2006/0074025 | A1 | 4/2006 | Quay et al. | 514/12 |

OTHER PUBLICATIONS

Vemula, P. K., Li, J., John, G. (2006) Enzyme Catalysis: Tool to Make and Break Amygdalin Hydrogelators from Renewable Resources: A Delivery Model for Hydrophobic Drugs. Journal of the American Chemical Society, vol. 128, p. 8932-8938.*
PCT International Preliminary Report on Patentability and PCT Written Opinion of the International Searching Authority, mailed Dec. 11, 2008 from WIPO OMPI, 34, chemin des Colombettes, 1211 Geneve 20, Suisse.

* cited by examiner

*Primary Examiner* — Scarlett Goon
(74) *Attorney, Agent, or Firm* — Hoffman & Baron, LLP

(57) ABSTRACT

A method for preparing hydro/organo gelators from disaccharide sugars by biocatalysis and their use in enzyme-triggered drug delivery. Controlled delivery of an anti-inflammatory, chemopreventive drug is achieved by an enzyme-triggered drug release mechanism via degradation of encapsulated hydrogels. The hydro- and organo-gelators are synthesized in high yields from renewable resources by using a regioselective enzyme catalysis and a known chemopreventive and anti-inflammatory drug, curcumin, is encapsulated in the gel matrix and released by enzyme triggered delivery. The release of the drug occurs at the physiological temperature and control of the drug release rate is achieved by manipulating the enzyme concentration and temperature. The by-products formed after the gel degradation clearly demonstrated the site specificity of degradation of the gelator by enzyme catalysis. The present invention has applications in developing cost effective, controlled drug delivery vehicles from renewable resources, with a potential impact on pharmaceutical research and molecular design and delivery strategies.

5 Claims, 13 Drawing Sheets

TABLE 1 - Gelation Ability of Amygdalin Derivatives 1-3 in Various Solvents

Gelator = 0.01-2 wt%

| solvent | derivative | | |
| --- | --- | --- | --- |
| | 1 | 2 | 3 |
| water | S | G | G |
| methanol | S | G | G |
| ethanol | S | G | G |
| acetonitrile | G | PG | PG |
| ethyl acetate | G | G | G |
| carbon tetrachloride | P | G | G |
| benzene | P | G | G |
| toluene | P | G | G |
| xylene | P | G | G |
| nonane | P | P | G |
| cyclohexane | I | Tp | Tp |

G = gel, PG = partial gel, P = precipitate, S = soluble, Tp = turbid precipitate, I = insoluble

FIG. 3

TABLE 1 - Effect of Enzyme Concentration and Temperature on Drug Release Time

Drug release was monitored by the UV-absorption spectra of curcumin

| enzyme concentration | temperature (°C) | drug release time (mins) | |
| --- | --- | --- | --- |
| | | for 5% release | for 1005 release |
| high (100 KLU/g) | 25 | - | - |
| | 37 | 120 | 720 |
| | 45 | 30 | 270 |
| low (10 KLU/g) | 25 | - | - |
| | 37 | 300 | 4320 |
| | 45 | 180 | 2880 |

FIG. 10

TABLE 3 - Crystallographic Parameters of Derivative 1

| crystal data | derivative 1 |
| --- | --- |
| empirical formula | $C_{24}H_{39}NO_{15}$ |
| formula weight | 581.56 |
| crystal size (mm) | 0.4 X 0.2 X 0.15 |
| crystal color | colorless |
| crystal system | monoclinic |
| space group | P2(1) |
| a, Å | 4.9484(11) |
| b, Å | 16.839(4) |
| c, Å | 17.249(4) |
| α/° | 90.00 |
| β/° | 91.455(8) |
| γ/° | 90.00 |
| Volume, Å$^{-3}$ | 1436.9(6) |
| Z | 2 |
| Dcalc | 1.344 |
| F(000) | 620 |
| μ Mo, Kα (mm$^{-1}$) | 0.112 |
| temperature (K) | 173(2) |
| total reflections | 4031 |
| observed reflection [$I>2\sigma(I)$] | 3260 |
| parameters refined | 400 |

FIG. 13

METHOD FOR PREPARING HYDRO/ORGANO GELATORS FROM DISACCHARIDE SUGARS BY BIOCATALYSIS AND THEIR USE IN ENZYME-TRIGGERED DRUG DELIVERY

This patent application is a continuation application of international patent application number PCT/US2007/012333, filed on May 22, 2007, for a METHOD FOR PREPARING HYDRO/ORGANO GELATORS FROM DISACCHARIDE SUGARS BY BIOCATALYSIS AND THEIR USE IN ENZYME-TRIGGERED DRUG DELIVERY, which claims priority based on U.S. provisional patent application No. 60/802,412, filed on May 22, 2006, for a METHOD FOR PREPARING HYDRO/ORGANO GELATORS FROM DISACCHARIDE SUGARS BY BIOCATALYSIS AND THEIR USE IN ENZYME-TRIGGERED DRUG DELIVERY, both patent applications are incorporated herein by reference.

BACKGROUND OF THE INVENTION

1. Field of the Invention

The present invention relates to hydro/organo gelators, and more particularly, the present invention relates to a method for preparing hydro/organo gelators from disaccharide sugars by biocatalysis and their use in enzyme-triggered drug delivery, cosmetic components delivery, and making of templated materials to generate inorganic and soft nanomaterials.

2. Description of the Prior Art

Use of renewable resources for production of valuable chemical commodities is becoming a topic of great interest and an objective of promoting the industrial bio-refinery concept in which a wide array of valuable chemicals, fuel, food, nutraceuticals, and animal feed products all result from the integrated processing of grains, oil seeds, and other biomass materials.[1]

[1] Lorenz, P. & Zinke, H. White biotechnology: differences in US approaches? *Trends Biotechnol.* 23, 570-574 (2005); Business and regulatory news. OECD says industrial biotech not realizing potential. *Nat. Biotechnol.* 19, 493-494 (2001).

An article by Stephan Harrera[2] illustrates that industrial or 'white' biotechnology[3] is making an increasingly important contribution to the development of a sustainable, biobased economy by an environmental benign approach.[4] It uses enzymes and micro-organisms to make products in sectors, such as chemistry, food and feed, paper, textile, and medicine. As opposed to chemical synthesis, enzyme catalysis is highly selective and has been used to generate various specialty chemicals,[5] including sugar-based esters.[6]

[2] Herrera, S. Industrial biotechnology-a chance at redemption. *Nat Biotechnol.* 22, 671-675 (2004).
[3] Industrial biotechnology and sustainable chemistry. *Royal Belgian Academy of Applied Sciences*, Brussels (January 2004).
[4] Eissen, M., Metzger, J. O., Schmidt, E. & Schneidewind, U. 10 Years after rio-concepts on the contribution of chemistry to a sustainable development. *Angew. Chem. Int. Ed* 41, 414-436 (2002); Biermann, U. et al. New synthesis with oils and fats as renewable raw materials for the chemical industry. *Angew. Chem. Int. Ed.* 39, 2206-2224 (2000); Gibson, J. M. et al. Benzene-free synthesis of phenol. *Angew. Chem. Int. Ed.* 40, 1945-1948 (2001).
[5] Wandrey, C., Liese, A. & Kihumbu, D. Industrial biocatalysis: past, present and future. *Org. Process Res. Dev.* 4, 286-290 (2000).
[6] Yan, Y., Bornscheuer, U. T. & Schmid, R. D. Lipase-catalyzed synthesis of vitamin C esters. *Biotechnol. Lett.* 21, 1051-1054 (1999).

Thus, there exists a need for developing building blocks from renewable resources to generate soft nanomaterials, such as new surfactants, liquid crystals, organic gelling materials, and hydrogels.[7]

[7] John, G., Masuda, M. & Shimizu, T. Nanotube formation from renewable resources via coiled nanofibers. *Adv. Mater.* 13, 715-718 (2001); John, G., Masuda, M., Jung, J. H., Yoshida, K. & Shimizu, T. Unsaturation influenced gelation of aryl glycolipids. *Langmuir* 20, 2060-2065 (2004); John, G., Mason, M., Ajayan, P. M. & Dordick, J. S. Lipid-based nanotubes as functional architectures with embedded fluorescence and recognition capabilities. *J. Am. Chem. Soc.* 126, 15012-15013 (2004).

Hydrogels have a range of biomedical applications in areas such as tissue engineering,[8] controlled released drug delivery systems,[9] and medical implants.[10] Design and synthesis of low-molecular-weight hydrogelators has received considerable attention in soft materials research in terms of its potential applications in cosmetics, toiletries, and pharmaceutical formulations. Literature study reveals that there are only limited reports on easily achievable and efficient low-molecular-weight gelators that are able to gel water or even water mixtures with other solvents,[11] and which are often achieved by multi-step chemical synthesis. Surprisingly, to the best of applicants' knowledge, to date there are no examples in the literature where low-molecular-weight hydrogelators were synthesized from renewable resources by using regioselective enzyme catalysis.

[8] Lee, K. Y. & Mooney, D. J. Hydrogels for tissue engineering. *Chem. Rev.* 101, 1869-1879 (2001).
[9] Friggeri, A., Feringa, B. L. & van Esch, J. Entrapment and release of quinoline derivatives using a hydrogel of low molecular weight gelator. *J. Controlled Release* 97, 241-248 (2004); Yang, Z., Liang, G., Wang, L. & Xu, B. Using a kinase/phosphatase switch to regulate a supramolecular hydrogel and forming the supramolecular hydrogel in vivo. *J. Am. Chem. Soc.* DOI:10.1021/j057412y (2006); van Bommel, K. J. C., Stuart, M. C. A., Feringa, B. L. & van Esch, J. Two-stage enzyme mediated drug release from LMWG hydrogels. *Org. Biomol. Chem.* 3, 2917-2920 (2005).
[10] Lee, K. Y. & Mooney, D. J. Hydrogels for tissue engineering. *Chem. Rev.* 101, 1869-1879 (2001); Miyata, T., Uragami, T. & Nakamae, K. Biomolecule-sensitive hydrogel. *Adv. Drug Delivery Rev.* 54, 79-98 (2002).
[11] Menger, F. M. & Caran, K. L. Anatomy of a gel. Amino acid derivatives that rigidify water at submillimolar concentrations. *J. Am. Chem. Soc.* 122, 11679-11691 (2000); Jokic, M., Makarevic, J., Zinic, M. & Makarevic, J. A novel type of small organic gelators: bis(amido acid) oxalyl amides. *J. Chem. Soc., Chem. Commun.* 1723-1724 (1995); Makarevie, J. et al. Bis(amino acid) oxalyl amides as ambidextrous gelators of water and organic solvents: supramolecular gels with temperature dependent assembly/dissolution equilibrium. *Chem. Eur. J.* 7, 3328-3341 (2001); Oda, R., Huc, I. & Candau, S. J. Gemini surfactants as new, low molecular weight gelators of organic solvents and water. *Angew. Chem. Int. Ed.* 37, 2689-2691 (1998); Estroff, L. A. & Hamilton, A. D. Effective gelation of water using a series of bis-urea dicarboxylic acids. *Angew. Chem. Int. Ed.* 39, 3447-3450 (2000); Kobayashi, H. et al. Molecular design of "super" hydrogelators: understanding the gelation process of azobenzene-based sugar derivatives in water. *Org. Lett.* 4, 1423-1426 (2002); Luboradzki, R., Gronwald, O., Ikeda, M., Shinkai, S. & Reinhoudt, D. N. An attempt to predict the gelation ability of hydrogen-bond-based gelators utilizing a glycoside library. *Tetrahedron* 56, 9595-9599 (2000); Gronwald, 0. & Shinkai, S. Sugar-integrated gelators of organic solvents. *Chem. Eur. J.* 7, 4328-4334 (2001); Jung, J. H. et al. Self-assembly of a sugar-based gelator in water: Its remarkable diversity in gelation ability and aggregate structures. *Langmuir* 17, 7229-7232 (2001); Wang, G. & Hamilton, A. D. Low molecular weight organogelators for water. *Chem. Commun.* 310-311 (2003).

Thus, there exists a need to use biocatalysis as a tool to make gelators from biomass and their assembly to form hierarchical superstructures in water, i.e., formation of hydrogel and soft nanomaterials, encapsulation of hydrophobic drug or hydrophobic cosmetic components, as well as enzyme mediated hydrogel degradation, which will give new insights into low-molecular-weight hydrogelators-based drug delivery.

Controlled delivery of drugs or cosmetic material occurs when a polymer, whether natural or synthetic, is judiciously combined with a drug or other active agent in such a way that the active agent is released in a pre-designed manner.[12] While these advantages can be significant, the potential disadvantages cannot be ignored, such as the possible toxicity or non-biocompatibility of the materials used, the undesirable by-products from gel degradation, and the higher cost of controlled-release systems compared with traditional pharmaceutical formulations.

[12] Dorski, C. M., Doyle, F. J. & Peppas, N. A. Preparation and characterization of glucose-sensitive P(MMA-a-EG)hydrogels. *Polym. Mater. Sci. Eng. Proceed.* 76, 281-282 (1997); Vert, M., Li, S. & Garreau, H. More about the degradation of LA/GA derived matrices in aqueous media. *J. Controlled Release* 16, 15-26 (1991).

Thus, there exists a need for sugar amphiphiles by regioselective synthesis of amygdalin esters as new hydrogelators, which are low cost, efficient, safe, and with high gelation efficiency.

[O-β-D-glucopyranosyl-(1-6)-β-D-glucopyranosyloxy] benzeneacetonitrile known as D-Amygdalin is a naturally occurring glycoside found in many food plants, for example, the kernels of apples, almonds, peaches, cherries, and apricots.[13] Amygdalin (a by-product of apricot, almonds and peach industry, see FIG. 1, which are pictures of: (a) an apricot pit that is a source of amygdalin; (b) *Curcuma longa*; and, (c) powdered curcumin[14] that is commonly known as turmeric and used in traditional Indian culinary and medicine—has been used as a main ingredient in commercial preparations of laetrile, a purported therapeutic agent.[15]

[13]Jones, D. A. Why are so many food plants are cyanogenic? *Phytochemistry* 47, 155-162 (1998).
[14]Curcumin is just one example as a drug model.
[15]Turczan, J. W. & Medwick, T. Qualitative and quantitative analysis of amygdalin using NMR spectroscopy. *Anal. Lett.* 10, 581-590 (1977); Syrigos, K. N., Rowlinson-Busza, G. & Epenetos, A. A. In vitro cytotoxicity following specific activation of amygdalin by β-glucosidase conjugated to a bladder cancer-associated monoclonal antibody. *Int. J. Cancer* 78, 712-719 (1998).

Thus, there exists a need to synthesize amygdalin derivatives that can form nanoaggregates through self-assembly and encapsulation of a hydrophobic drug followed by release of the encapsulated drug upon enzyme mediated degradation, i.e., enzyme-triggered drug-delivery.

In amygdalin-fatty acid conjugates, sugar moiety can facilitate the stacking of molecules through hydrogen bonding, phenyl ring can facilitate intermolecular interactions through π-π stacking, and hydrophobic hydrocarbon chain not only decreases the solubility in water, it also helps the molecular association through the van der Waals interactions.

In general, multi-step synthesis, arduous separation procedures, and lower yields often keep low-molecular-weight gelators away from commercial use due to high production cost. Strikingly, the hydrogelators of the present invention were synthesized from renewable resources in a single-step process in high yields (>90%), and unpurified crude products showed unprecedented gelation abilities like their counter pure products, allowing the development of versatile gelators which can be made from low cost starting materials and without purification.

Thus, there exists a need for gelator molecules with various chain lengths. See FIG. 2, which is a synthetic scheme of amygdalin-based amphiphiles.

SUMMARY OF THE INVENTION

Thus, an object of the present invention is to provide a method for preparing hydro/organo gelators from disaccharide sugars by biocatalysis and their use in enzyme-triggered drug delivery, which avoids the disadvantages of the prior art.

Briefly stated, another object of the present invention is to provide a method for preparing hydro/organo gelators from disaccharide sugars by biocatalysis and their use in enzyme-triggered drug delivery. Controlled delivery of an anti-inflammatory, chemopreventive drug is achieved by an enzyme-triggered drug release mechanism via degradation of encapsulated hydrogels. The hydro- and organo-gelators are synthesized in high yields from renewable resources by using a regioselective enzyme catalysis and a known chemopreventive and anti-inflammatory drug, curcumin, is encapsulated in the gel matrix and released by enzyme triggered delivery. The release of the drug occurs at the physiological temperature, and control of the drug release rate is achieved by manipulating the enzyme concentration and temperature. The by-products formed after the gel degradation clearly demonstrate the site specificity of degradation of the gelator by enzyme catalysis. The present invention has applications in developing cost effective, controlled drug delivery vehicles from renewable resources, with a potential impact on pharmaceutical research and molecular design and delivery strategies.

The novel features considered characteristic of the present invention are set forth in the appended claims. The invention itself, however, both as to its construction and its method of operation together with additional objects and advantages thereof will be best understood from the following description of the specific embodiments when read and understood in connection with the accompanying drawing.

Another object of the present invention is to provide a method for preparing hydro/organo gelators from disaccharide sugars by biocatalysis and their use in enzyme-triggered or thermo-triggered cosmetic delivery. Controlled delivery of components of cosmetic formula is achieved by an enzyme-triggered release mechanism via degradation of encapsulated hydrogels. The hydro- and organo-gelators are synthesized in high yields from renewable resources by using a regioselective enzyme catalysis. The release of the cosmetic components occurs at the physiological temperature and control of their release rate is achieved by manipulating the enzyme concentration and temperature. The present invention has applications in developing cost effective, controlled cosmetic delivery vehicles from renewable resources.

Another object of the present invention is to provide a method for preparing hydro/organo gelators from disaccharide sugars by biocatalysis and their use in making templated materials to develop inorganic nanomaterials.

BRIEF DESCRIPTION OF THE DRAWING

The figures of the drawing are briefly described as follows:

FIG. 3 is a table of gelation ability of amygdalin derivatives 1-3 in various solvents;

FIG. 10 is a table of the effect of enzyme concentration and temperature on drug release time;

FIG. 13 is a table of the crystallographic parameters of derivative 1.

DETAILED DESCRIPTION OF THE PREFERRED EMBODIMENT

Synthesis of Hydrogelators by Enzyme Catalysis

By taking advantage of the supreme control on regioselectivity of enzyme catalysis, a series of amygdalin derivatives were made where selectively introduced acyl moiety on primary hydroxyl group gave excellent yields.

Figure 2:
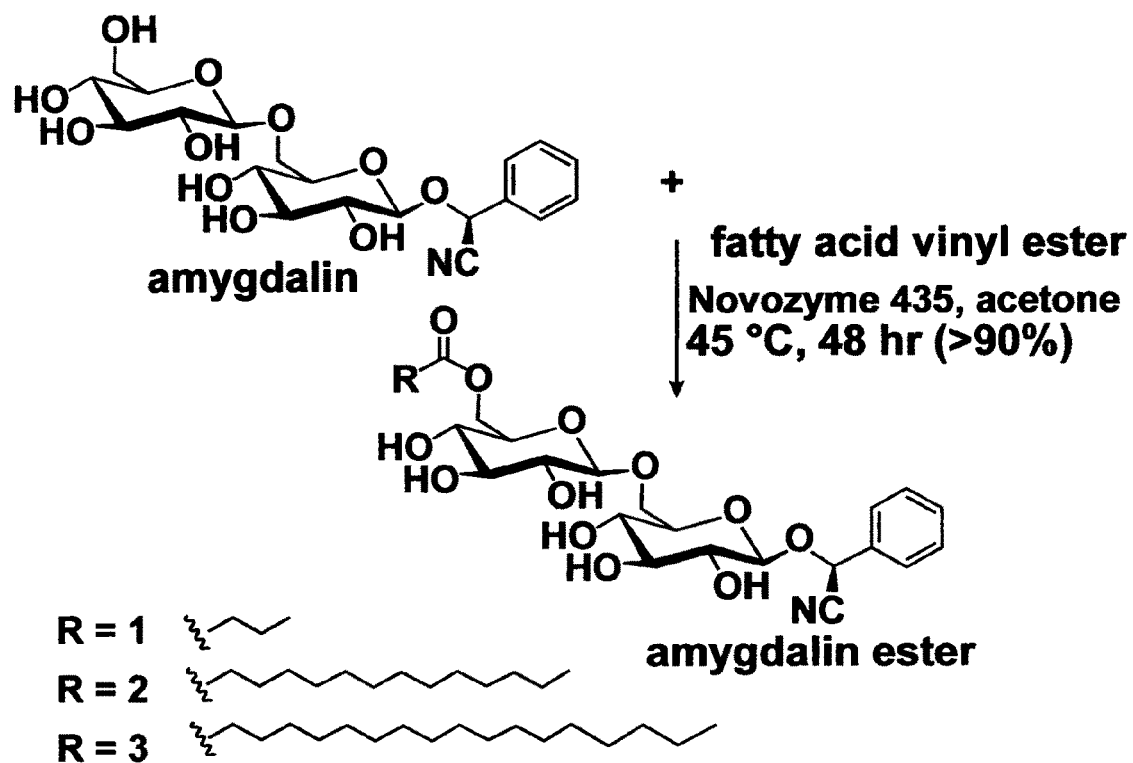
FIG. 2 is a synthetic scheme of amygdalin-based amphiphiles.

Amygdalin is a disaccharide containing one primary hydroxyl group that forms ester bonds with fatty acids. Vinyl esters were used as acyl donors. The detailed synthesis procedures are shown in the METHODS section below and the synthetic route to the amphiphilic amygdalin derivatives is shown FIG. 2.

In general, multi-step synthesis, arduous separation procedures, and lower yields often keep low-molecular-weight gelators away from commercial use due to high production cost.[16] Strikingly, the hydrogelators of the present invention were synthesized from renewable resources in a single-step process in high yields (>90%), and unpurified crude products showed unprecedented gelation abilities like their counter pure products, allowing the development of versatile gelators which can be made from low cost starting materials and without purification. In particular, this property gives the opportunity to develop these gelators in industrial scales for various applications in cosmetics, toiletries, drug deliveries, nanomaterials, and pharmaceutical formulations.[17]

[16]Zhang, S. Hydrogels: Wet or let die. *Nat. Mater.* 3, 7-8 (2004).
[17]Id.

Gelation Abilities of Derivatives 1-3

Amygdalin derivatives 1-3 encompass all required functional groups, such as hydrogen bond forming 'sugar' headgroup, phenyl ring for π-π stacking, and hydrocarbon chain for van der Waals interactions. These groups together can synergistically act to form strong intermolecular interactions leading to the gelation. The gelation abilities of the derivatives 1-3 in water and in organic—polar and nonpolar—solvents are compared in FIG. 3, which is a table of gelation ability of amygdalin derivatives 1-3 in various solvents.

Typically, a gelator (0.01-2 mg) in a required solvent (0.1-1 mL) was heated until the solid was completely dissolved. The resulting solution was slowly allowed to cool to room temperature and gelation was visually observed. The gel sample obtained exhibited no gravitational flow in an inverted tube. All gels obtained were thermally reversible. Above their gelation temperature, the gels dissolved in water but could be returned to their original gel state upon cooling.

The amygdalin amphiphiles derivatives 1-3 showed unprecedented gelation abilities in a broad range of solvents at extremely low concentrations [0.05-0.2 wt % (MGC)], while displaying excellent thermal and temporal stabilities.

Scanning Electron Microscopic Studies

Figure 4:
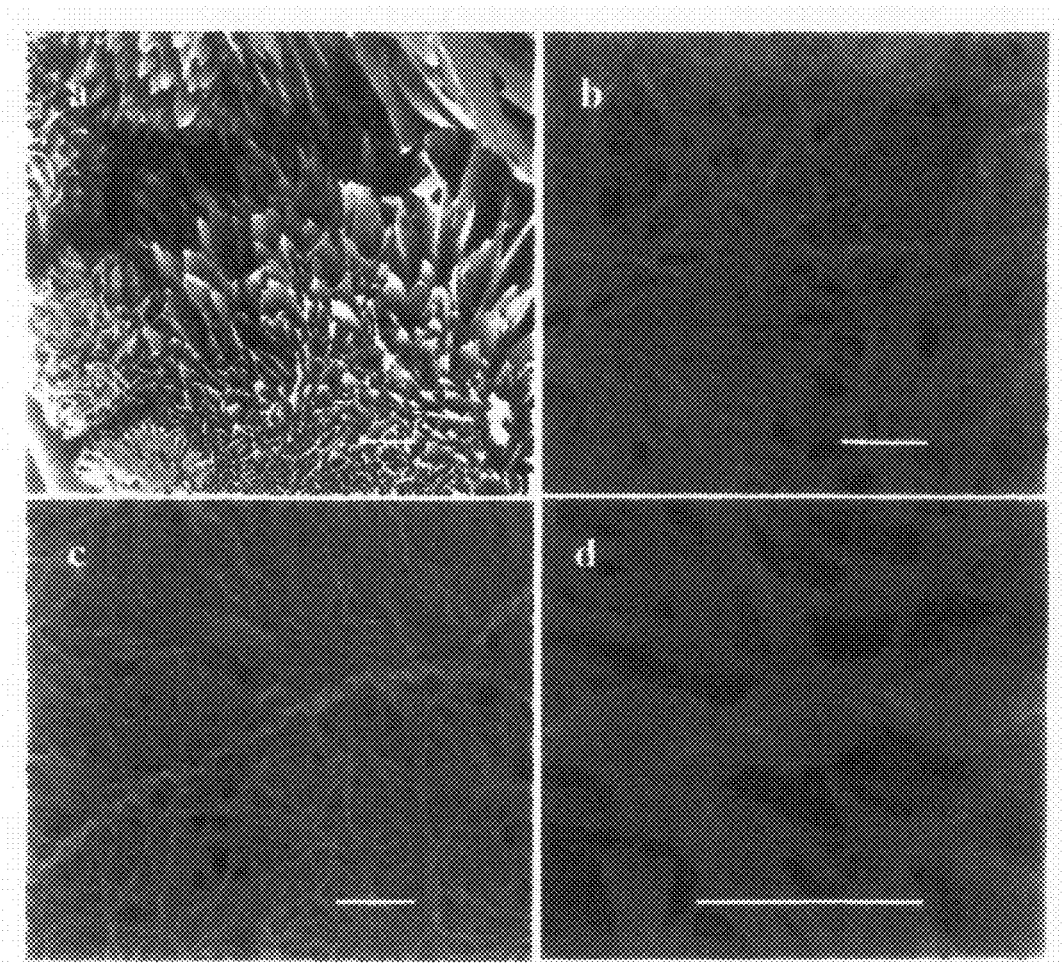
FIG. 4 are SEM micrographs, wherein scale bar is equivalent to 1 μM, of: (a) the organogel of derivative 1 prepared from acetonitrile; (b) the aqueous gel from derivative 2; (c) the aqueous gel from derivative 3; and, (d) a higher magnification of hydrogel derivative 2.

Molecular self-aggregation features can be observed on an electron microscope, since the initial stage of physical gelation is the self-assembly of gelator monomers. FIG. 4, which are SEM micrographs, wherein scale bar is equivalent to 1 μM, of: (a) the organogel of derivative 1 prepared from acetonitrile; (b) the aqueous gel from derivative 2; (c) the aqueous gel from derivative 3; and, (d) a higher magnification of hydrogel derivative 2—presents the scanning electron microscope (SEM) images of the organogels formed by derivative 1 shown in FIG. 4(*a*) and the aqueous gels formed by derivatives 2 and 3 shown in FIGS. 4(*b*) and (*c*), respectively.

Figure 5:
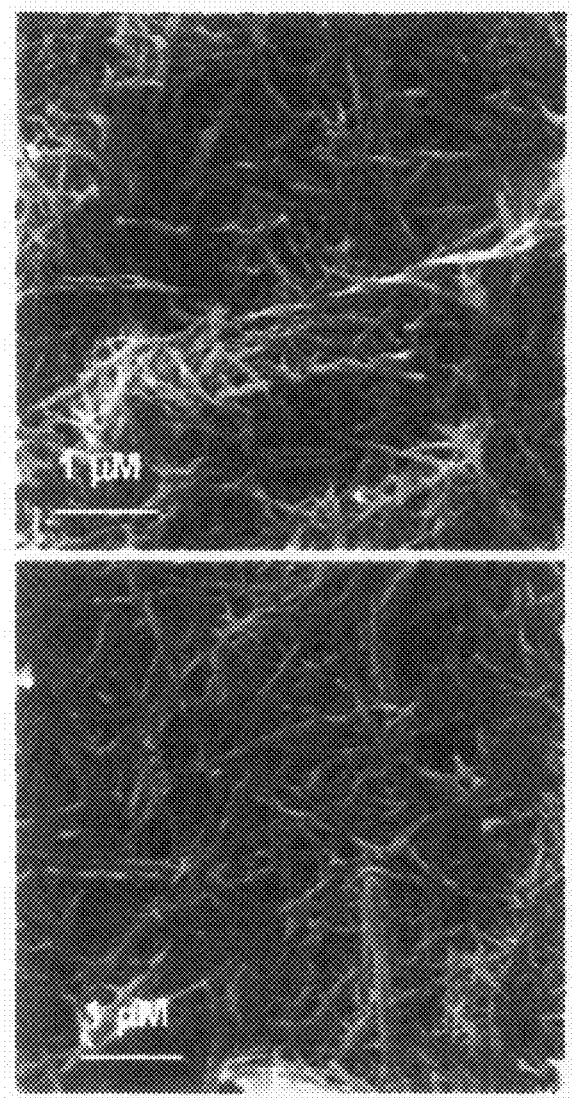
FIG. 5 are scanning electron micrographs of curcumin-embedded hydrogels of derivative 3.

The images of their xerogels reveal two different types of morphologies. The organogel formed in acetonitrile by derivative 1 showed 'grass' like morphology. Hydrogels of derivatives 2 and 3 showed helical ribbon morphology at microscopic level. Analysis of these aggregates clearly showed that the individual fibers are approximately 50 nm in width, about 100-125 nm in pitch, and up to several micrometers in length. These helical nanofibers are entangled and formed a dense fibrous network resulting in immobilization of the solvent. Gels were also made in the presence of the drug curcumin, and SEM images suggest that inclusion of curcumin does not change the basic twisted fibrous morphology of the hydrogel. See FIG. 5, which are scanning electron micrographs of curcumin embedded hydrogels of derivative 3.

XRD Measurements and Crystal Structure Analysis

Figure 6:
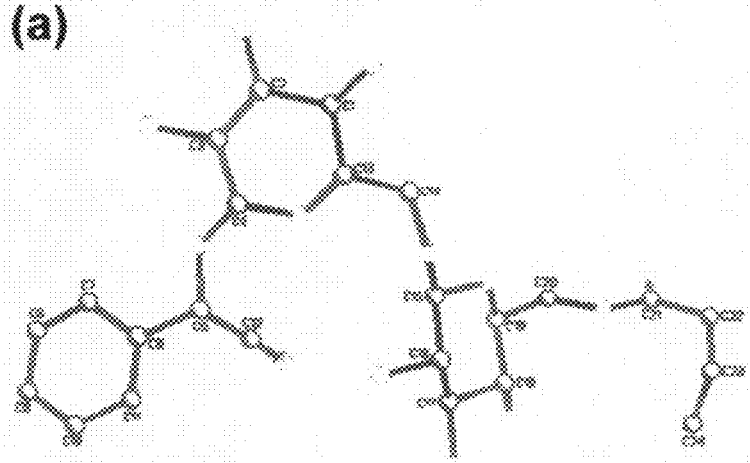
FIG. 6 are: (a) the crystal structure analysis of derivative 1 in water; and, (b) a top view showing the π-π stacking of phenyl rings and hydrogen boding between two amygdalin molecules, wherein hydrogen bonding acts as a bridge between the stacked amygdalin molecules along the b-axis shown as blue arrows and between these two stacks along the a-axis shown as black arrows, and wherein: oxygen is shown as red; nitrogen is shown as blue; carbon is shown as white circles; and, hydrogen-bonding is shown as black dashed lines.
Figure 6:
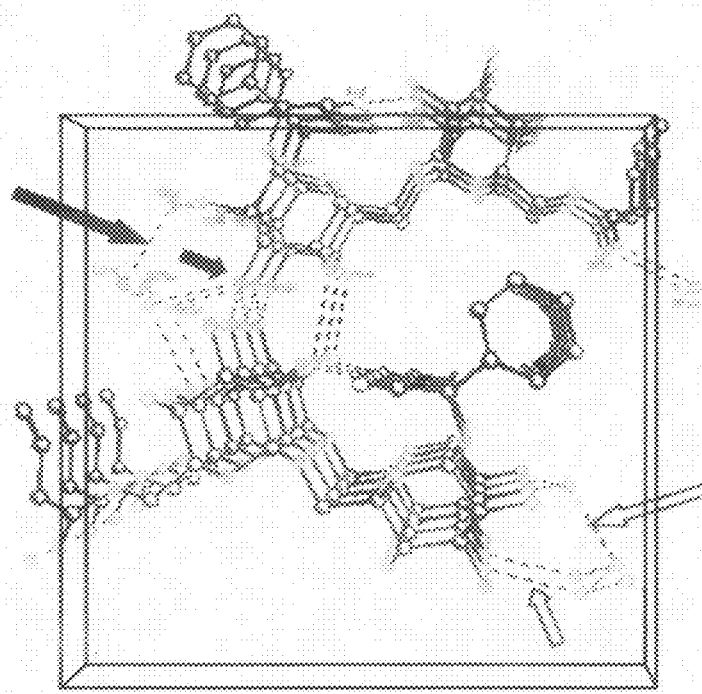

From X-ray diffraction patterns of the xerogels of derivatives 1-3 prepared from xylene and water, the long spacings (d) were calculated and discussed to postulate the possible mode of aggregation in the gel state. Possibly lamellar structures were formed by these amphiphiles in gels. The xerogels of derivatives 1-3 were prepared by a freezing-and-pumping method and were sponge-like materials. Amygdalin butyrate (derivative 1) gave a single crystal in water that was successfully analyzed by X-ray crystallography. The crystal structure of derivative 1 is shown in FIG. 6, which are: (a) the crystal structure analysis of derivative 1 in water; and, (b) a top view showing the π-π stacking of phenyl rings and hydrogen boding between two amygdalin molecules, wherein hydrogen bonding acts as a bridge between the stacked amygdalin molecules along the b-axis shown as blue arrows and between these two stacks along the a-axis shown as black arrows, and wherein: oxygen is shown as red; nitrogen is shown as blue; carbon is shown as white circles; and, hydrogen-bonding is shown as black dashed lines. The information obtained from the single crystal analysis was combined with the XRD data to postulate possible molecular packing of amygdalin amphiphiles within the hydro- and organogels.

Drug Encapsulation and Enzyme Triggered Controlled Release

Figure 1:
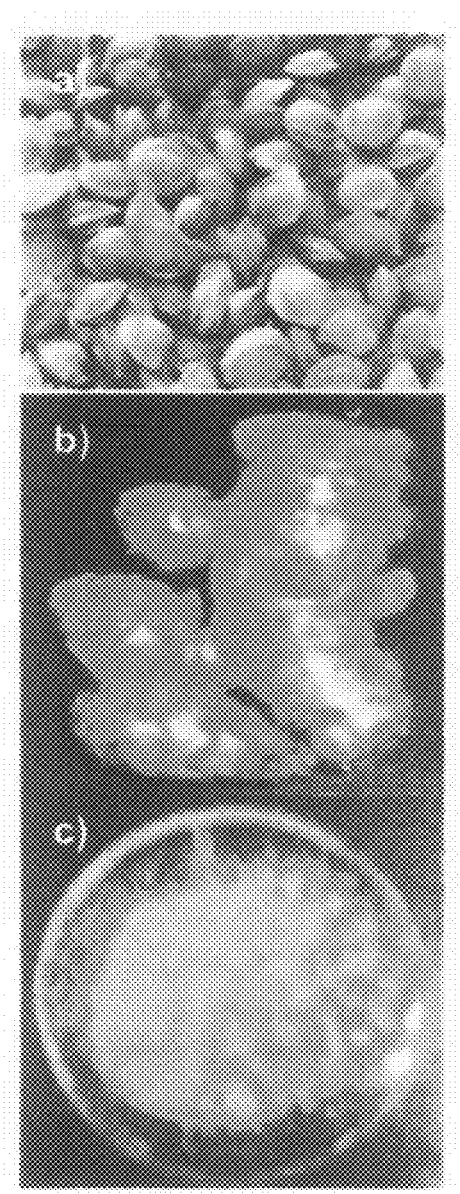
FIG. 1 are pictures of: (a) an apricot pit that is a source of amygdalin; (b) *Curcuma longa*; and, (c) powdered curcumin that is commonly known as turmeric and used in traditional Indian culinary and medicine. It is also a known chemopreventive and anti-inflammatory drug.

Solubilization of hydrophobic drugs and developing suitable drug delivery systems is a challenging task in drug discovery research.[18] A conceptual approach of single-step enzyme-triggered drug delivery at physiological conditions was performed where a hydrophobic drug molecule was encapsulated—solubilized without chemical modification—in a hydrogel and subsequent release of the drug by breaking the gel by using hydrolase enzyme (Lipolase 100L, Type EX). The preformed hydrogel was degraded completely by the lipolase while the encapsulated chemopreventive hydrophobic drug curcumin was released. See FIGS. 1(b) and (c) for images of curcumin. Drug release was monitored by absorbance spectra of the drug. Control of the drug release rate was achieved by manipulating the enzyme concentration and/or temperature. The by-products formed after the gel degradation were characterized and the cleavage site of the gelator by enzyme was determined. Gel degradation occurred due to the cleavage of the ester bond in the gelator by the hydrolase enzyme.

[18]Miyata, T., Uragami, T. & Nakamae, K. Biomolecule-sensitive hydrogel. *Adv. Drug Delivery Rev.* 54, 79-98 (2002).

Discussion

Gelation is the delicate balance between solubility and precipitation. To obtain this, the structural features in the gelator molecules need to be fined tuned.

The amphiphiles of derivatives 1-3 were generated by attaching a fatty acid chain to amygdalin via regiospecific transesterification reaction on a primary sugar hydroxyl. Inspection of FIG. 3 reveals that the amygdalin derivatives are versatile gelators for water and polar/nonpolar organic solvents, derivative 1 formed gels in two solvents out of ten tested, whereas derivative 3 gelled in all ten solvents. This explains the importance of chain length on gelation ability. Noteworthy to mention is that derivatives 2 and 3 did not require any co-solvent to form the hydrogel despite their gelation ability in less polar solvents like benzene, toluene, and xylene. These gelators showed excellent gelation in a broad range of solvents.

Robustness of a gelator can be determined by considering three parameters: i) gelation ability in a broad range of solvents; ii) low minimum gelation concentration (MGC); and, iii) thermal stability of the gels.

For example, these gelators—derivatives 2 and 3—formed gels in highly polar solvents like water, methanol, and nonpolar solvents like nonane, benzene, and toluene. Minimum gelation concentration (MGC) of these gels are very low, typically 0.05 and 0.2 wt % for derivative 3 in water and benzene, respectively. This is one of the lowest gelation concentrations reported in the literature for any class of gelators.[19] Similarly, the other derivatives also exhibit lower MGC values for various solvents typically between 0.07 to 0.5 wt %. In addition, they show good thermal and temporal stabilities.

[19]van Bommel, K. J. C., Stuart, M. C. A., Feringa, B. L. & van Esch, J. Two-stage enzyme mediated drug release from LMWG hydrogels. *Org. Biomol. Chem.* 3, 2917-2920 (2005); Kobayashi, H. et al. Molecular design of "super" hydrogelators: understanding the gelation process of azobenzene-based sugar derivatives in water. *Org. Lett.* 4, 1423-1426 (2002).

Gel to solution transition temperature ($T_{gel}$) was determined by typical 'inversion tube method'[20] and from differential scanning calorimeter (DSC). The $T_{gel}$ values of these gels were in the range of 40 to 85° C. for 0.5 wt % gels depending on the solvent used. All gels were stable for months. Hence, together satisfying all three parameters, the reported amygdalin based gelators could be considered as excellent gelators.

[20]Menger, F. M. & Caran, K. L. Anatomy of a gel. Amino acid derivatives that rigidify water at submillimolar concentrations. *J. Am. Chem. Soc.* 122, 11679-11691 (2000).

Figure 7:
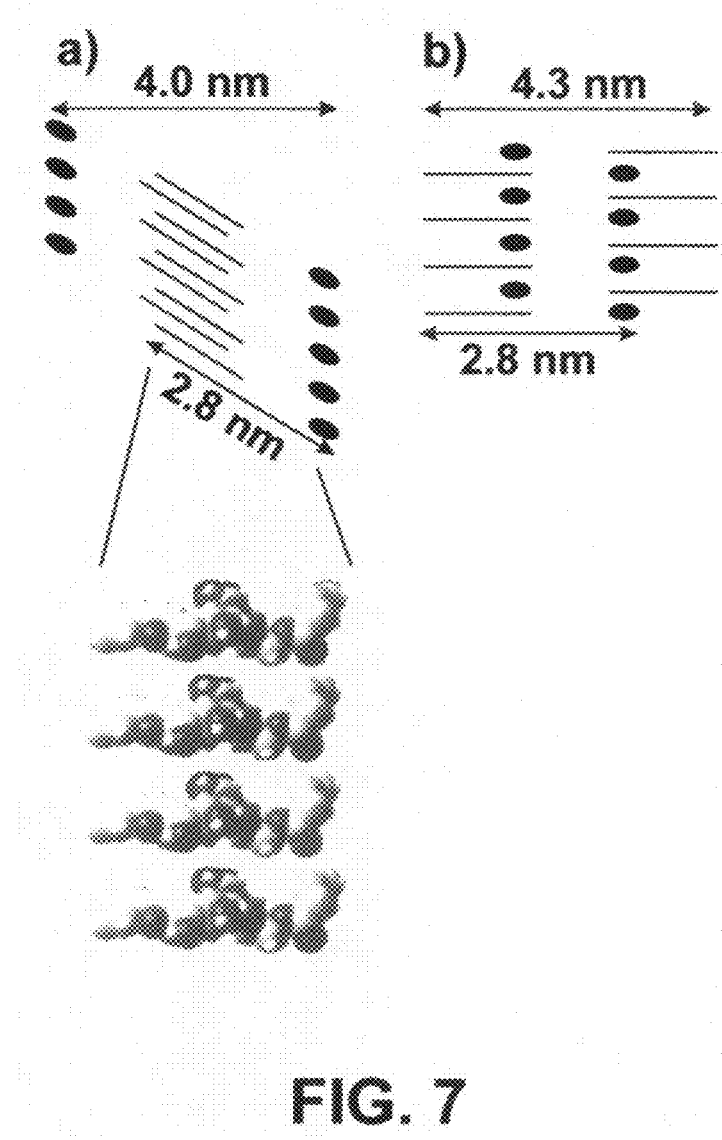
FIG. 7 are schematic representations of possible molecular packing models for the: (a) hydrogels; and, (b) organogels of derivative 2.

In X-ray diffraction experiments, p-xylene gel of derivative 2 showed long distance spacing of 4.3 nm, which is higher than the molecular length—2.8 nm from the optimized geometry calculations—and much lower than double that of the extended molecular length of derivative 2. Thus, there could be two possible ways to explain how these molecules could form self-assembly, which is shown in FIGS. 7(a) and (b), which are schematic representations of possible molecular packing models for the: (a) hydrogels; and, (b) organogels of derivative 2. First, a highly interdigitated bilayer structure with the alkyl chain tilting with respect to the normal to the layer plane shown in FIG. 7(a), and second, the hydrophilic parts face inside the assembly and hydrophobic chains are exposed to the outer side of the assembly shown in FIG. 7(b). On the other hand, the long distance spacing for the hydrogel of derivative 2 is 4.0 nm strongly supports that interdigitated molecular packing would be possible at the nanoscopic level. It is unlikely that hydroxyls containing sugar headgroup will face inside and lipophilic hydrocarbon chains face bull polar solvent, hence model shown in FIG. 7(b) would be ruled out. Thus, molecular packing in the hydrogels of derivative 2 would be similar to that shown in FIG. 7(a). In this model, hydrophilic groups are exposed to the outer solvent while hydrophobic chains are highly interdigitated, which is consistent with previous reports.[21] On the basis of long distance spacing of the hydro- and organogels of derivative 3, it is proposed that most likely the molecular packing of the amphiphiles are similar to the gels of 2 and it might be possible that in the case of the gels of derivative 3, the allyl chain tilt would be more than that of derivative 2. Therefore, layered structures for self-assembly of these gels are also supported by their solid-state crystal structure.

[21]John, G., Masuda, M. & Shimizu, T. Nanotube formation from renewable resources via coiled nanofibers. *Adv. Mater.* 13, 715-718 (2001); Gronwald, O. & Shinkai, S. Sugar-integrated gelators of organic solvents. *Chem. Eur. J.* 7, 4328-4334 (2001).

Amygdalin butyrate—derivative 1—gives single crystals in water. The isolated single crystal was successfully analyzed by X-ray crystallography. Interestingly, these molecules were well packed in the crystal lattice due to the extensive hydrogen bonding. Strong well-arranged intra- and inter-molecular hydrogen bonding was observed. Intramolecular hydrogen bonding between N (nitrogen) of the nitrile group and of sugar hydroxyl (O—H) hydrogen helps to form a locked conformation that apparently participated in forming the stacked structures.

Stacked layered structure was stabilized by π-π stacking and van der Waals interactions between the alkyl chains. These two stacks were arranged in 'head-to-tail' fashion to give the extended porous structure shown in FIG. 6(b).

Water molecules were involved in two types of hydrogen bonding. In one type, water molecules formed hydrogen bonding with sugar hydroxyls while acting as bridged molecules between stacked amygdalin amphiphiles and stabilized the stacked layers as shown in open arrows in FIG. 6(b). In the second mode, water molecules were involved in hydrogen bonding with sugar hydroxyls while acting as bridged molecules between two different stacks of amygdalin amphiphiles to stabilize the two adjacent layers as shown in filled arrow in FIG. 6(b). In addition to that, the intermolecular hydrogen bonding between sugar hydroxyls of two amygdalin molecules from opposite stacks, which also indicates the greater ability to form self-assembled structures by amygdalin derivatives, was observed.

By collecting the information from the crystal structure of derivative 1, most likely in the gel state similar self-assembly would be possible. Previously in literature two reports explained the aggregation modes of the gelators based on single crystal analysis.[22] As evidenced in the crystal structure, there are several interactions, such as extensive hydrogen bonding, π-π stacking, and van der Waals interactions existing. Such cooperative interactions play an important role in stabilizing the fiber structures in the gel state.

[22] Kiyonaka, S. et al. Semi-wet peptide protein array using supramolecular hydrogel. *Nat. Mater.* 3, 58-64 (2004); Kumar, D. K., Jose, D. A., Das, A. & Dastidar, P. First snapshot of a nonpolymeric hydrogelator interacting with its gelling solvents. *Chem. Commun.* 32, 4059-4062 (2005).

The possible applications of these robust gels to utilize the hydrophobic pockets within the gel to encapsulate hydrophobic drugs were investigated. Hence, these hydrogels were tested as a drug delivery vehicle model. In the process of developing drug delivery systems, chemical modification of the drug and cleavage induced by external stimuli, such as increasing temperature followed by enzyme-mediated cleavage, has been shown recently.[23] Such an approach has limitations when applying to different drugs. Covalently connecting the drugs to the hydrogelators may not be achievable trivially in all types of drugs. In the process of chemical modification, there is a potential chance of loosing its original drug activity. It would be an ideal system to have encapsulated drug models, where drug release can be triggered by enzymes without the need of altering pH or temperature. An enzyme triggered drug delivery at physiological condition was demonstrated where a hydrophobic drug molecule was encapsulated—solubilized without chemical modification—in an hydrogel. Subsequent release of the drug was by breaking the gel with an hydrolase enzyme (Lipolase 100L, Type EX).

[23] van Bommel, K. J. C., Stuart, M. C. A., Feringa, B. L. & van Esch, J. Two-stage enzyme mediated drug release from LMWG hydrogels. *Org. Biomol. Chem.* 3, 2917-2920 (2005).

The success of this approach in drug delivery model systems for possible in vivo applications rely on a few factors, such as: (a) selected hydrogels should be able to provide the hydrophobic pockets to solubilize the hydrophobic drugs; (b) gel degradation—to release the drug—should take place at mild conditions like physiological pH and temperature; and, (c) the products formed after degradation should be biocompatible.

Selected as a model drug was one of the best-characterized chemopreventive agents, curcumin—or diferuloylmethane[24]—extracted from the root of *Curcuma longa*, which presents strong anti-oxidative, anti-inflammatory, and antiseptic properties.[25] In addition, curcumin also inhibits purified human immunodeficiency virus type 1 (HIV-1) integrace,[26] HIV-1 and HIV-2 proteases,[27] and HIV-1 long terminal repeat-directed gene expression of acutely or chronically infected HIV-1 cells.[28] Despite such astounding drug activity, unfortunately curcumin has an extremely low aqueous solubility and poor bioavailability limiting its pharmaceutical use.[29] One possible way to increase its aqueous solubility is to form inclusion complexes, i.e. to encapsulate curcumin as a guest within the internal cavities of a water-soluble host or encapsulate within the nanoaggregates—formed by self-assembly—that have hydrophobic pockets within.

[24] Duvoix, A. et al. Chemopreventive and therapeutic effects of curcumin. *Cancer Lett.* 223, 181-190 (2005).
[25] Hergenhahn, M. et al. The chemopreventive compound curcumin is an efficient inhibitor of Epstein-Barr virus BZLF1 transcription in Raji DR-LUC cells. *Mol. Carcinog.* 33, 137-145 (2002).
[26] Hergenhahn, M. et al. The chemopreventive compound curcumin is an efficient inhibitor of Epstein-Barr virus BZLF1 transcription in Raji DR-LUC cells. *Mol. Carcinog.* 33, 137-145 (2002); Mazumder, A., Raghavan, K., Weinstein, J., Kohn, K. W. & Pommier, Y. Inhibition of human immunodeficiency virus type-1 integrase by curcumin. *Biochem. Pharm.* 49, 1165-1170 (1995).
[27] Burke, T. R. Jr. et al. Hydroxylated aromatic inhibitor of HIV-1 integrase. *J. Med. Chem.* 38, 4171-4178 (1995).
[28] Sui, Z., Salto, R., Li. J., Craik, C. & Ortiz de Montellano, P. R. Inhibition of the HIV-1 and HIV-2 proteases by curcumin and curcumin boron complexes. *Bioorg. Med. Chem.* 1, 415-422 (1993).
[29] Khodpe, S. M., Priyadarsini, K. I., Palit, D. K. & Mukherjee, T. Effect of solvent on the excited-state photophysical properties of curcumin. *Photochem. Photohiol.* 72, 625-631 (2000).

Figure 8:
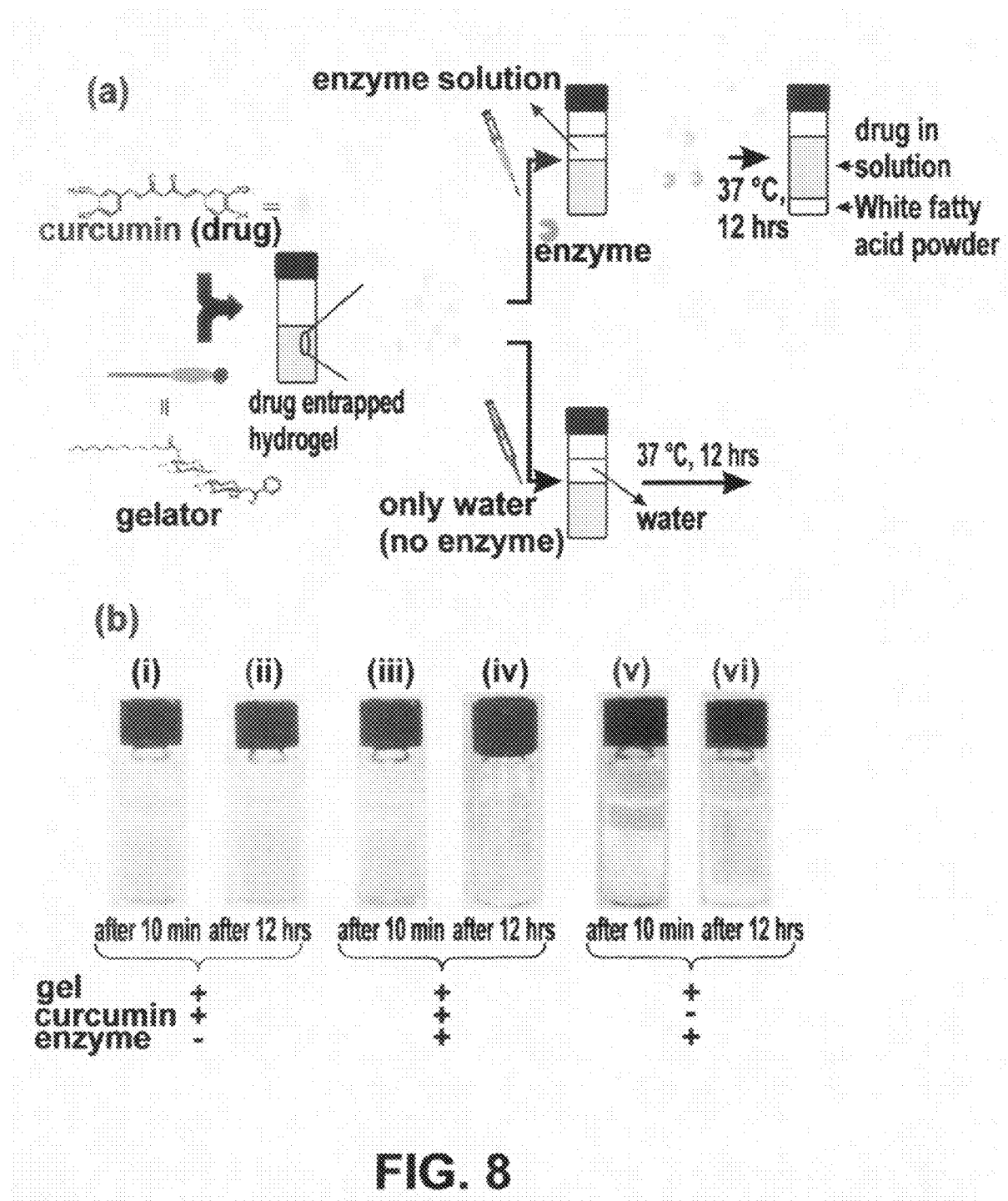
FIG. 8 are: (a) a schematic representation of drug encapsulation in a supramolecular hydrogel and subsequent release of the drug by enzyme mediated degradation of hydrogel at physiological temperature; and, (b) real images of the hydrogels of derivative 3 with (i-iv) and without (v-vi) curcumin, wherein after complete gel degradation, the remained white fluffy powder that settled at the bottom was characterized as a water insoluble fatty acid that formed after gel degradation by the enzyme.

Schematic representation of curcumin encapsulation and enzyme-mediated release is depicted in FIG. 8(a) wherein FIG. 8 are (a) a schematic representation of drug encapsulation in a supramolecular hydrogel and subsequent release of the drug by enzyme-mediated degradation of hydrogel at physiological temperature; and, (b) real images of the hydrogels of derivative 3 with (I-iv) and without (v-vi) curcumin, wherein after complete gel degradation, the remained white fluffy powder that settled at the bottom was characterized as a water insoluble fatty acid that formed after gel degradation by the enzyme. The release of curcumin into the solution in the presence of enzyme was monitored by measuring the curcumin UV-absorption spectrum. The absorption spectrum recorded in aqueous gel solution was compared with the curcumin spectra recorded in methanol. The effect of solvent polarity on the absorbance spectrum of curcumin has previously been reported as minimal.[30] High concentration of curcumin ($1\times10^{-3}$ M) was solubilized in 0.5 wt % hydrogel of derivative 3—reported[31] solubility of curcumin in water is $3\times10^{-8}$ M, i.e., ~33,000 times more than solubilized in the hydrogel. The resulted gel was yellow in color as shown in FIG. 8(b), and due to the hydrophobic nature, curcumin might be located at hydrophobic pockets of the gel. To test this hypothesis, water was added to the preformed gel and left for 12 hrs. The UV-absorption of the supernatant was recorded. Absence of any absorbance peak concluded the unavailability of curcumin on the gel surface by adsorption.

[30] Id.
[31] Tonnesen, H. H., Másson, M. & Loftsson, T. Studies of curcumin and curcuminoids. XXVII. Cyclodextrin complexation: solubility, chemical and photochemical stability. *Int. J. Pharm.* 244, 127-135 (2002).

Figure 9:
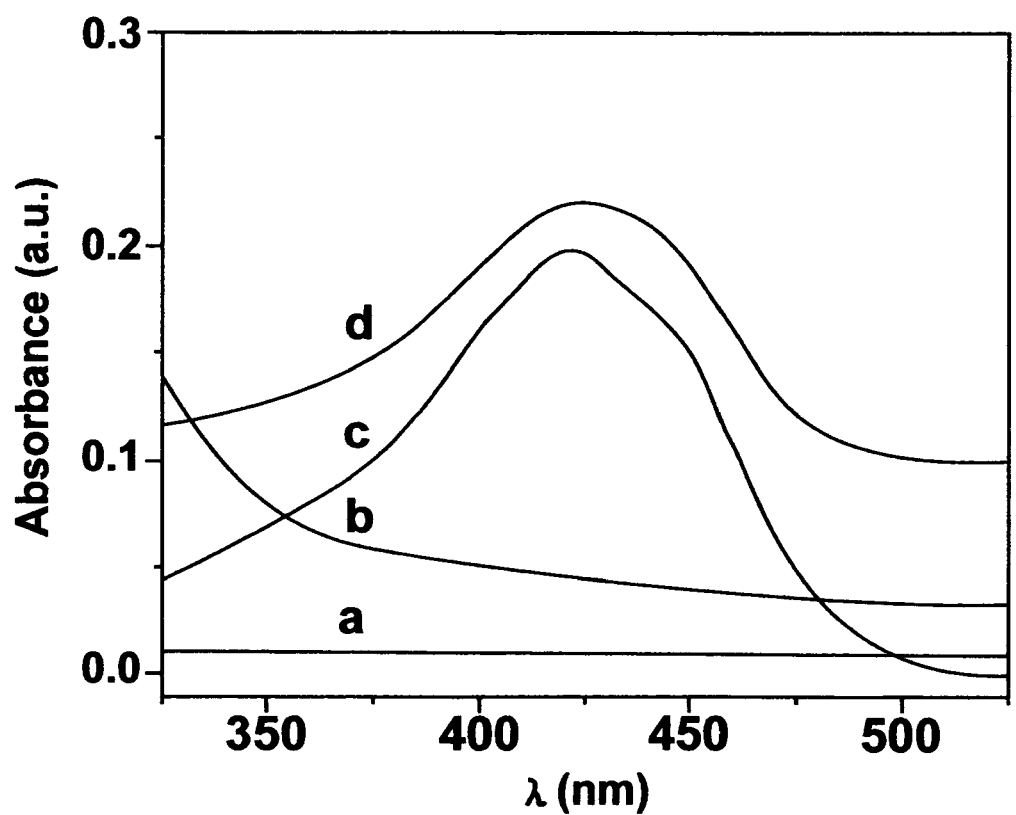
FIG. 9 are UV absorption spectra of curcumin in various types of solution mixtures, including: (a) an curcumin-entrapped hydrogel in the presence of an enzyme; (b) an enzyme added to the hydrogel that does not contain curcumin; (c) an curcumin-entrapped hydrogel in the absence of an enzyme; and, (d) a methanolic solution of curcumin.

First, 0.5 mL of lipase—Lipolase 100L, Type EX, lipase units 100 KLU/g—was added to the preformed gel and kept at 37° C.—far lower than gel melting temperature. Initially the added solution was colorless as shown in FIG. 8(b)(iii). After 12 hrs visual changes occurred as shown in FIG. 8(b)(iv), i.e., 100% of the gel has been degraded and the top solution has became yellow in color, which indicates that upon enzyme mediated gel degradation, encapsulated curcumin has been released into the solution. This was confirmed by spectroscopic experiments. Aliquots were collected after addition of an enzyme to the hydrogel after 10 min and 12 hrs and absorbance spectrum were recorded. Interestingly, initial aliquots after 10 min did not show any absorbance peak, but aliquots collected after 12 hrs showed absorption maxima at 425 nm, which corresponds to the absorption peak of curcumin. See FIG. 9, which are UV absorption spectra of curcumin in various types of solution mixtures, including: (a) an curcumin-entrapped hydrogel in the presence of an enzyme; (b) an enzyme added to the hydrogel that does not contain curcumin; (c) an curcumin-entrapped hydrogel in the absence of an enzyme; and, (d) a methanolic solution of curcumin.

To find out the role of the enzyme on hydrogel degradation, similar experiments were carried out by adding only water without an enzyme. As expected, the curcumin-encapsulated gel was still intact after incubating for a few days at 37° C. There was no visual change in the gel volume and in the added solution. See FIG. 8(b). And, the absorbance peak corresponding to the curcumin was not shown. See FIG. 9(a). In addition, control experiments with the same hydrogel of derivative 3 without curcumin, which is opaque and white in color as shown in FIG. 8(b), were performed. To this, 0.5 mL of lipolase was added and incubated at 37° C. After 12 hrs, the gel degraded completely. The absorption spectrum of the solution shown in FIG. 9(b) was then recorded. Absence of the absorption peak at 425 nm suggested that the previously observed peak, FIG. 9(c), corresponded to the curcumin released into the solution.

To obtain control on the rate of release, the role of enzyme concentration and temperature on gel degradation or controlled drug release was investigated. In a first set of experiments, the temperature was changed while keeping enzyme concentration constant. After addition of the enzyme to the preformed gel, the vial was kept at room temperature for two days, and as explained previously, curcumin release was monitored by absorption spectra. Interestingly, even after two days at room temperature in the presence of the enzyme, there was no gel degradation observed, and thus, there was no release of encapsulated curcumin. When the vial was placed at 37° C. in an incubator, after 120 min slow release of curcumin was observed, and within 720 min encapsulated curcumin was released completely. Similarly when incubated at 45° C., release was initiated within 30 min and complete release was observed in 270 min.

Figure 11:
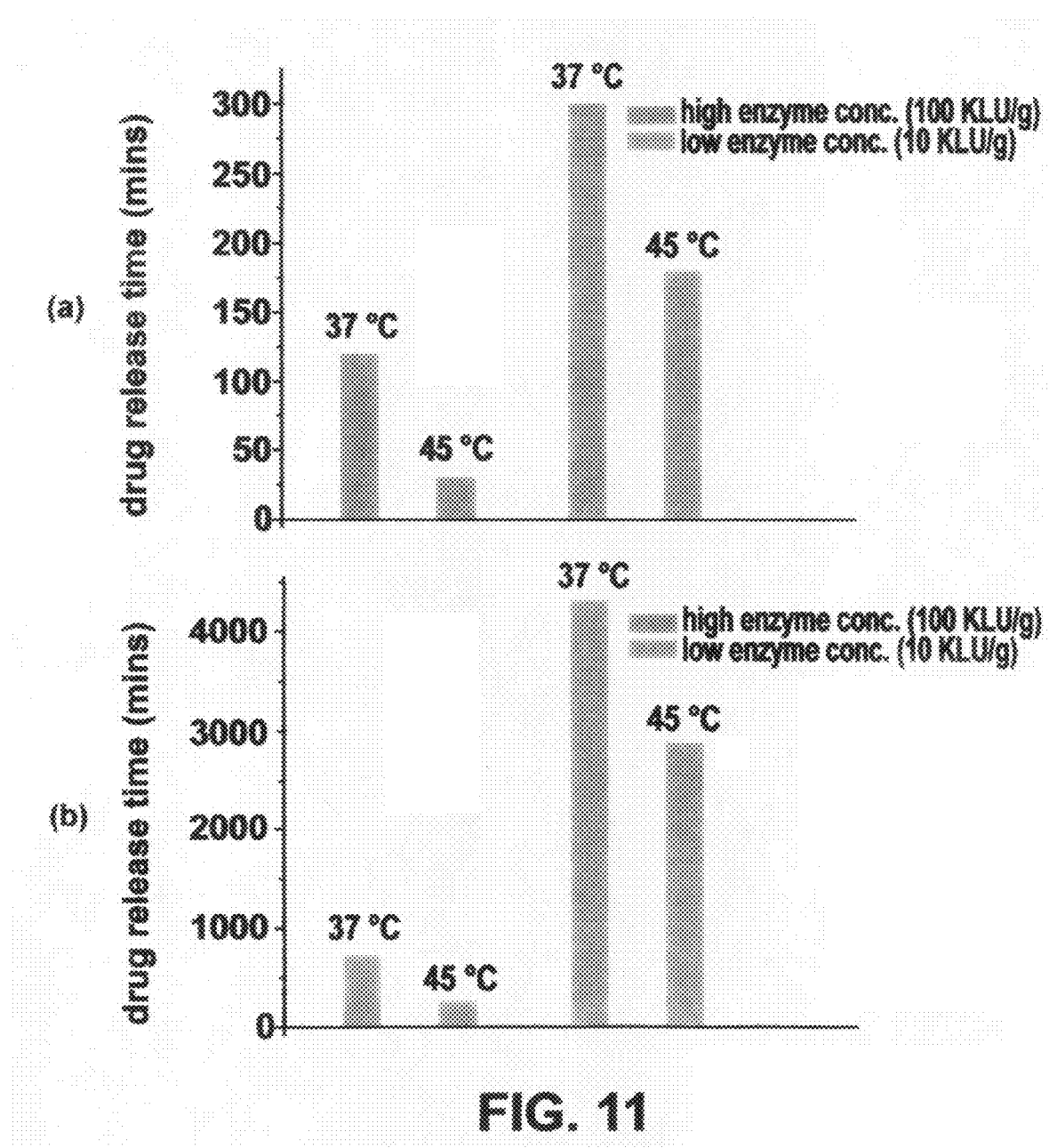
FIG. 11 are a comparison of curcumin-drug-release time at different concentrations and different temperatures from hydrogels of amygdalin derivatives by enzyme degradation, wherein: (a) is the time required for 5% release; and, (b) is the time required for 100%.

In a second set of experiments, the enzyme concentration was changed while keeping the temperature constant. 10 times lower concentrated lipolase—units 10 KLU/g—added to the preformed curcumin encapsulated gel. At room temperature, even after several days, there was no release. Then the vial was placed at 37° C. in incubation and took 300 min to start the drug release, which eventually took 4,320 min to release completely. In addition to this, a similar low enzyme concentrated vial was directly incubated at 45° C. In this case, drug release was started after 180 min and in 2,880 min complete release was observed. Hence at constant temperature, drug release can be controlled by lowering the enzyme concentration. These results are summarized in FIG. 10, which is a table of the effect of enzyme concentration and temperature on drug release time, and FIG. 11, which are a comparison of curcumin-drug-release time at different concentrations and different temperatures from hydrogels of amygdalin derivatives by enzyme degradation, wherein: (a) is the time required for 5% release; and, (b) is the time required for 100%—which clearly demonstrate the achieved control over the release of an encapsulated drug from a hydrogel.

Figure 12:
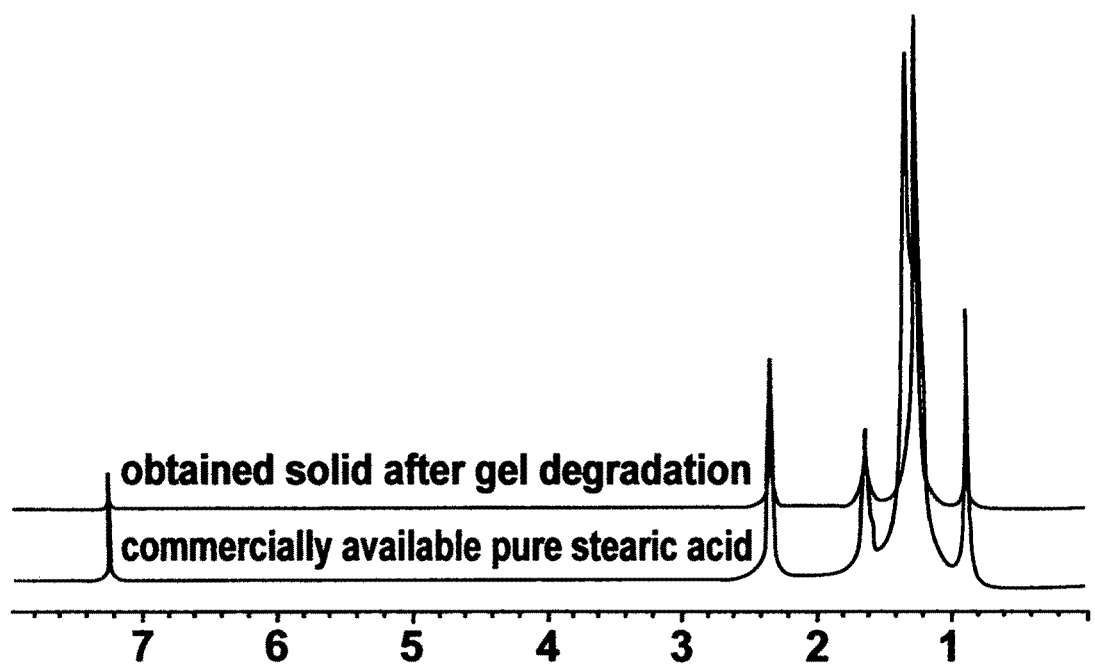
FIG. 12 is a comparison of the $^1$H-NMR spectra of commercially available stearic acid and the white fluffy solid obtained after gel degradation, which was filtered, freeze-dried, and NMR recorded in Chloroform.

It is important to characterize the products/compounds formed after gel degradation. To find out the other components formed after gel degradation, thin layer chromatography (TLC) of the solution was performed and it was found that this solution contains amygdalin, curcumin, and enzyme—confirmed by comparing $R_f$ values. This indicates that the enzyme is degrading the gel by cleaving the ester bond of derivative 3. Upon gel degradation, a white fluffy solid was produced, which is not soluble in water, and thus settled down in the vial. See FIG. 8(b)(iv). The solid was isolated and characterized by $^1$H-NMR, and it matched with the NMR of pure stearic acid. See FIG. 12, which is a comparison of the $^1$H-NMR spectra of commercially available stearic acid and the white fluffy solid obtained after gel degradation, which was filtered, freeze-dried, and NMR recorded in Chloroform. Hence, it is undoubtedly suggesting that gel degradation is occurring through the cleavage of the ester bond of amygdalin derivatives by lipolase enzyme.

These results unambiguously explain the drug encapsulation abilities of hydrogels formed by amygdalin derivatives and enzyme-triggered drug release. Noteworthy, these gelators were generated via enzyme catalysis, and gels were degraded—converting from gelators to starting materials—by yet again using enzyme catalysis in environmentally benign conditions.

Methods
General Information

Amygdalin and curcumin was purchased from Acros Chemicals (Fisher Scientific Company, Suwane, Ga.). The Novozyme 435 [lipase B from *Candida Antarctica*, (CALB)] and Lipolase 100L were obtained from Novozymes through Brenntag North America. Other reagents were obtained from TCI America (Portland, Oreg.).

General Synthesis Procedure of Amygdalin Esters by Enzyme Catalysis

Typically, 40 ml of acetone containing 0.1 mol/L amygdalin and 0.3 mol/L vinyl esters—vinyl butyrate, vinyl myristate, and vinyl stearate—was added to 1 g of Novozyme 435. The reaction mixtures were placed in an incubator and shook at 200 rpm at 45° C. for 48 hr. The reactions were terminated by the filtration of reaction mixtures. After evaporating the solvent, the obtained crude products were purified by silica gel flash chromatography using ethyl acetate—methanol (4:1) as eluent, afforded pure products as white solids. The yields were above 90% for all reactions.

Amygdalin Butyrate—Derivative 1

$^1$H-NMR, (Acetone-$d_6$, 300 MHz) δ 7.58 (m, 2H), 7.48 (m, 2H), 7.46 (m, 1H), 5.98 (s, 1H), 5.1-5.33 (br m, 6H), 4.45 (d, 1H), 4.29 (d, 1H), 4.22 (dd, 1H), 4.04 (dd, 1H), 3.99 (dd, 1H), 3.59 (dd, 1H), 3.38 (m, 1H), 3.35 (m, 1H), 3.25 (m, 2H), 3.18 (m, 2H), 3.13 (m, 1H), 3.1 (m, 1H), 2.2 (t, 2H), 1.24 (m, 2H), 0.83 (t, 3H). Anal. Calcd. for $C_{24}H_{33}NO_{12}$: C, 54.64; H, 6.31; N, 2.66. Found: C, 54.68; H, 6.30; N. 2.70.

Amygdalin Tetradecanoate—Derivative 2

$^1$H-NMR, (CDCl$_3$, 300 MHz) δ 7.58 (m, 2H), 7.48 (m, 2H), 7.46 (m, 1H), 5.98 (s, 1H), 5.1-5.33 (br m, 6H), 4.45 (d, 1H), 4.29 (d, 1H), 4.22 (dd, 1H), 4.04 (dd, 1H), 3.99 (dd, 1H), 3.59 (dd, 1H), 3.38 (m, 1H), 3.35 (m, 1H), 3.25 (m, 2H), 3.18 (m, 2H), 3.13 (m, 1H), 3.1 (m, 1H), 2.2 (t, 2H), 1.24 (m, 22H), 0.83 (t, 3H). Anal. Calcd. for $C_{34}H_{53}NO_{12}$: C, 61.15; H, 8.00; N, 2.10. Found: C, 61.20; H, 8.02; N. 2.14.

Amygdalin Octadecanoate—Derivative 3

$^1$H-NMR, (CDCl$_3$, 300 MHz) δ 7.58 (m, 2H), 7.48 (m, 2H), 7.46 (m, 1H), 5.98 (s, 1H), 5.1-5.33 (br m, 6H), 4.45 (d, 1H), 4.29 (d, 1H), 4.22 (dd, 1H), 4.04 (dd, 1H), 3.99 (dd, 1H), 3.59 (dd, 1H), 3.38 (m, 1H), 3.35 (m, 1H), 3.25 (m, 2H), 3.18 (m, 2H), 3.13 (m, 1H), 3.1 (m, 1H), 2.2 (t, 2H), 1.24 (m, 30H), 0.83 (t, 3H). Anal. Calcd. for $C_{38}H_{61}NO_{12}$: C, 63.05; H, 8.49; N, 1.93. Found: C, 63.11; H, 8.51; N. 1.95.

Preparation of Supramolecular Gels: Self-Assembly

Typically, the gelator (0.01-2 mg) and required solvent (0.1-1 mL) were placed into a 2 mL scintillation vial, which was then sealed with a screw cap. The vial was heated and shook until the solid was completely dissolved. The solution was set aside and allowed to cool to room temperature. Gelation was considered to have occurred when no gravitational flow in the inverted tube was observed.

Gel Melting Temperatures

The Gel to Sol transition temperature ($T_{gel}$) was determined by two methods. One was the typical 'inversion tube method',[32] where the gel was prepared in a 2 mL glass vial by dissolving a 0.5 wt % gelator in a required amount of solvent and closed with a tight screw cap. The vial was immersed in water 'up side down' and slowly heated. The temperature where the viscous gel melted and dropped down was considered as the $T_{gel}$. The second method, $T_{gel}$ was determined by using a Mettler DSC-822 Differential Scanning Calorimeter equipped with a nitrogen-gas intra cooling system. The gel was hermitically sealed in a silver pan and measured against a pan containing alumina as reference. Thermograms were recorded at a heating rate of 5° C./min. The $T_{gel}$ values determined by these two methods were identical.

[32]Menger, F. M. & Caran, K. L. Anatomy of a gel. Amino acid derivatives that rigidify water at submillimolar concentrations. *J. Am. Chem. Soc.* 122, 11679-11691 (2000).

Observation of Gel Structure by Microscopy

The xerogel samples were prepared by the freezing-and-pumping method from their gel phases below the sol-gel transition temperature. It is important to note that the SEM images of xerogels and the following drying under ambient condition show similar morphologies. Therefore, morphology with the gels dried under ambient conditions, which was called xerogels, was studied.

X-Ray Powder Diffraction (XRD)

XRD measurements were conducted using a Bruker AXS D-8 Discover with GADDS diffractometer using graded d-space elliptical side-by-side multilayer optics, monochromated Cu—Kα radiation (40 kV, 40 mA), and an imaging plate. The gels were used as prepared in the wet condition for the analysis. A small portion of the gel sample was transferred to the sample holder and sealed off immediately using capstone tape to avoid any drying off of the solvent. The typical exposure time was 1 min for self-assembled structures with a 100 mm camera length.

X-Ray Single Crystal Analysis

X-ray quality colorless single crystals of derivative 1 were obtained from water in a flat rod shape. X-ray diffraction data were collected using Mo—Kα (λ=0.7 107 Å) radiation on a graphite monochromatized Bruker X8 APEX II diffractometer at 173(2) K. Data collection, data reduction, and structure solution refinement were carried out using the software package of SHELX97.[33] All structures were solved by direct methods (S1R92) and refined in a routine manner. Non-hydrogen atoms were treated anisotropically. Whenever possible, the hydrogen atoms were located on a different Fourier map and refined. The crystallographic parameters are listed in FIG. 13, which is a table of the crystallographic parameters of derivative 1.

[33]Sheldrick, G. M. *SHELEXL-97, A program for crystal structure solution and refinement*; University of Göttingen: Göttingen, Germany, 1993.

CONCLUSIONS

In conclusion, hydro/organogelators from renewable resources were successfully developed. Low-molecular-weight hydrogelators were synthesized by regioselective enzyme catalysis for the first time. Yields were quantitative and crude reaction mixtures exhibited equally unprecedented gelation properties like their counter pure products. This capability may allow development of hydrogelators in industrial scale for future applications.[34] The hierarchical structural characteristic of supramolecular gels were clearly demonstrated and the self-assembly based on XRD and single crystal analysis were explained.

[34]Zhang, S. Hydrogels: Wet or let die. *Nat. Mater.* 3, 7-8 (2004).

The gel fibers were self-assembled and stabilized by various interactions, such as intra- and inter-molecular hydrogen bonding, π-π stacking, and van der Waals interactions. The encapsulation of chemopreventive curcumin in the hydrogel was shown, and enzyme-triggered gel degradation was performed to release the encapsulated drug into the solution at physiological temperature. Controlled drug release rate was achieved by manipulating the concentration of enzyme or temperature.

The by-products formed after gel degradation were characterized and clearly demonstrated the site specificity of degradation of the gelator by enzyme catalysis. Supramolecular chemistry is now a powerful strategy for developing new molecularly defined materials in material and medicinal science. This would be a possible model system for drug encapsulation and enzyme mediated delivery for in vivo formulations and may have potential applications in pharmaceutical research and molecular design of value added products from biobased materials, otherwise under utilized.

It will be understood that each of the elements described above or two or more together may also find a useful application in other types of constructions differing from the types described above.

While the invention has been illustrated and described as embodied in a method for preparing hydro/organo gelators from disaccharide sugars by biocatalysis and their use in enzyme-triggered drug delivery, however, it is not limited to the details shown, since it will be understood that various omissions, modifications, substitutions, and changes in the forms and details of the device illustrated and its operation can be made by those skilled in the art without departing in any way from the spirit of the present invention.

Without further analysis, the foregoing will so fully reveal the gist of the present invention that others can by applying current knowledge readily adapt it for various applications without omitting features that from the standpoint of prior art fairly constitute characteristics of the generic or specific aspects of the invention.

The invention claimed is:

1. A drug-delivery composition, comprising:
    a) a hydro/organo gel prepared by assembly of gelators to form nano-aggregates, wherein the gelator is prepared from an esterification reaction between amygdalin and a fatty acid; and
    b) a hydrophobic drug encapsulated in said gel; wherein said drug is capable of release upon enzyme mediated degradation of said gel.

2. The composition of claim 1, wherein the hydro/organo gel is prepared by self-assembly of the gelators.

3. The composition of claim 1, wherein the gelator is selected from the group consisting of amygdalin butyrate, amygdalin tetradecanoate, and amygdalin octadecanoate.

4. The composition of claim 1, wherein the hydrophobic drug is curcumin.

5. The composition of claim 2, wherein said gelator is prepared by a biosynthetic reaction.

* * * * *